United States Patent [19]

Heath et al.

[11] Patent Number: 5,068,798

[45] Date of Patent: Nov. 26, 1991

[54] PROCESS ENVIRONMENT MONITORING SYSTEM

[75] Inventors: Warren J. Heath, Marlboro; Rene J. Langner, Plainville; Charles A. Bell, Weston, all of Mass.

[73] Assignee: Precision Systems, Inc., Natick, Mass.

[21] Appl. No.: 319,139

[22] Filed: Mar. 3, 1989

[51] Int. Cl.$^5$ .......................................... G01N 31/00
[52] U.S. Cl. .................................... 364/497; 340/632; 356/437; 73/23.42
[58] Field of Search ................... 364/550, 413.02, 558, 364/500, 497; 340/632, 825.06, 825.07, 825.3, 825.31, 825.32, 825.34, 825.36, 825.5; 356/437, 439; 73/23

[56] References Cited

U.S. PATENT DOCUMENTS

| | | | |
|---|---|---|---|
| 4,326,940 | 4/1982 | Eckles et al. | 364/500 X |
| 4,384,925 | 5/1983 | Stetter et al. | 364/497 |
| 4,525,069 | 6/1985 | Tanaka et al. | 356/437 |
| 4,526,028 | 7/1985 | Hübner et al. | 73/23 |
| 4,621,334 | 11/1986 | Garcia | 340/825.3 |
| 4,720,807 | 1/1988 | Ferran et al. | 364/558 |
| 4,816,658 | 3/1989 | Khandwala et al. | 340/825.31 |
| 4,823,290 | 4/1989 | Fasack et al. | 364/550 |
| 4,839,640 | 6/1989 | Ozer et al. | 340/825.34 |
| 4,858,152 | 8/1989 | Estes | 364/550 |
| 4,866,594 | 9/1989 | David et al. | 340/825.06 |
| 4,924,417 | 5/1990 | Yuasa | 364/550 |
| 4,947,352 | 8/1990 | Jenkins | 364/558 |
| 4,958,295 | 9/1990 | Davidson et al. | 364/497 |

OTHER PUBLICATIONS

Midac Promotional Literature, Mar. 1988.
MDA Scientific Promotional Literature, Apr. 1988.
Foxboro Company Product Application Data, Jul. 1985, PAD Q8000-004.
Foxboro Company Production Application Data, Jul. 1985, PAD Q8000-001.
Foxboro Company Laboratory Application Data, Jul. 1985, LAD 001-002.
Foxboro Company Promotional Literature, Aug. 1988, Bulletin K-46A.
Foxboro Company Promotional Literature, Feb. 1986, Bulletin K-40A.
Foxboro Company Promotional Literature, Jun. 1985, Bulletin K-38.
Foxboro Company Promotional Literature, Sep. 1986, Bulletin K-35A.
Foxboro Company Promotional Literature, Apr. 1988, Bulletin KI-48.
Foxboro Company Promotional Literature, Oct. 1985, Bulletin K-41.
Nicolet Company Promotional Literature-Systems 740, (Excerpts from) Feb. 1989.
Nicolet Company Newsletter FT-IR Spectral Lines, vol. 10, No. 1, (Excerpts from) Mar. 1989.

Primary Examiner—Joseph L. Dixon

[57] ABSTRACT

A process environment monitoring system collects and tests air samples from a number of different sample locations. Each sample is drawn into a sample test chamber into which a beam of infrared light is directed from an infrared source. The beam is reflected off mirrors in the test chamber a number of times before it exits and is directed to an infrared detector. The detector identifies absorption peaks in the spectrum of the infrared beam to determine the presence of certain gases of interest in the test chamber. A host computer is provided to function in conjunction with a valve controller to make up a data processing unit. The data processing unit services a number of tasks to make the process environment monitor a fully integrated system. The system controls employee identification, alarm triggering, and automated system control, as well as a number of other functions. Different system access levels are provided, and identification and access level information may be input by the reading of an employee identification card by a magnetic card reader.

3 Claims, 4 Drawing Sheets

PROCESS ENVIRONMENT MONITORING SYSTEM

BACKGROUND OF THE INVENTION

The present invention relates to process environment air monitoring and, in particular, to the monitoring of such environments as hospital operating rooms and sterilization rooms. It has been found that low level contamination by vapors such as anesthesia gases in operating rooms or bone glue vapors in sterilization rooms can have detrimental effects on the personnel who have long term exposure. These effects include malignancies, birth defects, and other adverse medical conditions. Various regulatory agencies have recently been invoking stricter rules regarding the tolerance exposure level for hospital personnel to such vapor contamination. Sampling teams have been used to periodically come into hospitals and monitor gas exposure in the rooms where these dangerous vapors may exist. But such visits are expensive and consequently rare.

The use of monitoring equipment including infrared (IR) detection equipment has been suggested to detect the vapors. An infrared detection system utilizes the fact that many of these dangerous vapors have a peak in their absorption spectrum somewhere in the infrared range. Such systems are commonly known in the art and used in various vapor detection disciplines.

SUMMARY OF THE INVENTION

What the industry has failed to provide until now is an integrated system capable of handling the volume of sampling as well as the efficiency standards necessary in a hospital environment. With the great number of hospital personnel and the wide variety of air sampling tasks necessary to be performed, a system is required which can service a number of different sampling locations, where each location requires different standards from the system. To provide this level of system control and to be able to record the exposure time of many hospital personnel, a dedicated system with software control has been developed.

In accordance with the present invention, a process environment monitoring system comprises a test cell and an optical analyzer for providing an analysis of gas in the test cell. Also provided in the preferred embodiment are a data processing unit and an input device. The data processing unit controls the analyzer and stores test results while the input device identifies an individual entering the process environment and relays the identification to the data processing system. The data processing system is programmed to maintain a record of exposure of individuals in the process environment. The input device can be a card reader or other such identificatiion system.

In a further embodiment of the process environment monitoring system, an inaccessible storage unit stores software to control operation of the data processing unit. This software is stored such as to prevent its unauthorized modification. An accessible storage unit by which a user is able to provide input data to the data processing system is also provided. Finally, a boot storage unit causes loading of software from the inaccessible storage unit and not from the accessible storage unit as the system powers up. A system based on a general purpose computer may thus be dedicated to the monitoring function. This system may allow the data processing system, under software control, to recognize authorized access to the data processing unit by means of a card reader.

The process environment monitoring system may also include a local alarm indicator in the process environment and a remote alarm indicator remote from the process environment. A data processing unit for controlling the analyzer and storing test results triggers actuation of the local alarm indicator when the analyzer indicates the amount of a gas in the process environment has reached a low level alarm limit. Similarly, the data processing unit triggers actuation of the remote indicator when an intermediate level alarm limit less than a critical level is reached. The system may be organized such that the alarms triggered by the data processing unit can be disabled only after the data processing system recognizes an identification input of an authorized individual.

The data processing unit may control the analyzer and store test results while also controlling the display of test information on the monitor. Means responsive to the data processing unit are provided for disabling the monitor as the data processing unit continues analysis and storage of test results. When a display is provided, the data processing unit may periodically shift the display of test information on the screen of the monitor to prevent damage to the display screen with a static image.

The system can be configured such that the data processing unit displays test information on the monitor only after it recognizes an identification input of an authorized individual. The system may also be made to enable the monitor when the user provides an in put to the system. If a card reader is included with the system, this input may be in the form of a user placing a card in the card reader. A display monitor may also be enabled when the analyzer indicates that an alarm limit has been reached.

The preferred system further comprises a plurality of gas conduits of different lengths for drawing gas from remote process environments. Also included is a flow controller for controlling the introduction of gas through respective conduits to the test cell. The flow controller causes gas to be drawn through the conduits at different times and for different durations of time which may be matched to the flow rates of the conduits.

After an optical analysis of the gas in the test cell is performed, fluid communication may be opened between the test cell and an evacuated volume which is larger in size than the test cell. This step rapidly evacuates the test cell and minimizes the amount of purging required prior to the next test. A typical size for the evacuated volume may be between 4 and 10 times the size of the test cell. A purge gas is drawn through the test cell prior to drawing another sample of gas from the process environment into the test cell. The purge gas may optionally be drawn from the process environment.

In a process environment monitoring system, another method of testing gas from the process environment comprises drawing a sample of the gas from the process environment and pressurizing the sample to at least two atmospheres in a test cell. Under pressurization, an optical analysis is performed on the gas in the test cell, the gas thereafter being discharged from the test cell. The pressure to which the sample is pressurized may correspond to the sensitivity required of the analyzer performing the optical analysis. Successive samples may be drawn from different process environments, and the pressure to which the sample is pressurized may be set according to the source of the process environment sample.

DESCRIPTION OF A PREFERRED EMBODIMENT

Figure 1:
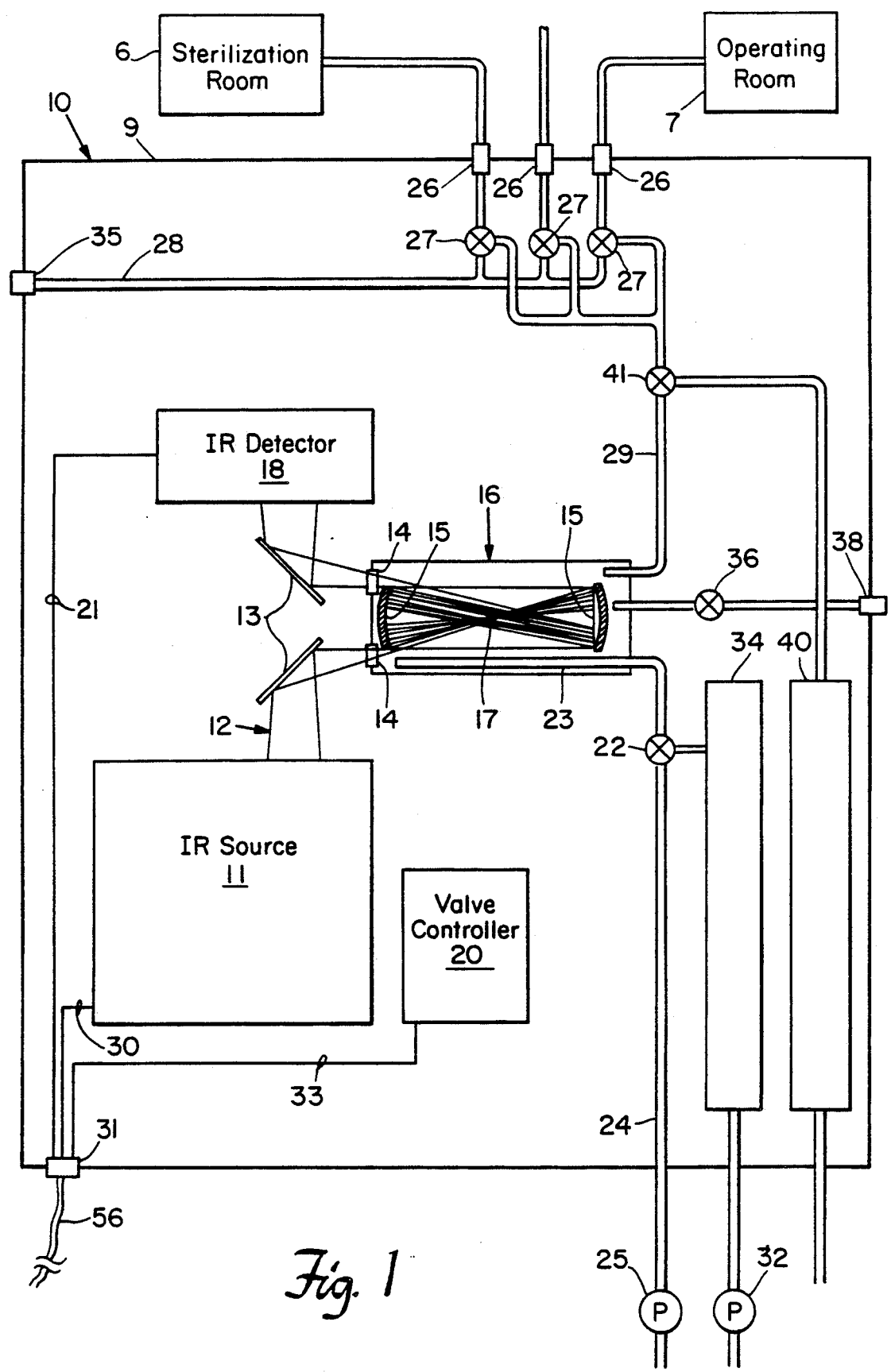
FIG. 1 shows the gas monitoring unit of the process environment monitoring system.

In FIG. 1 is shown a gas monitoring unit generally indicated at 10. This unit 10 is part of a system for environmental air monitoring such as might be used in a hospital operating room or sterilization room to detect an overabundance of certain harmful vapors. Enclosed in the outer casing 9 of gas monitoring unit 10 are the functional elements of the system. To test the air from a certain environment a sample is drawn into sample test chamber 16 through input tubing 29 from one of valves 27, each of which controls the flow through a sample tube leading to a different environmental location, such as sterilization room 6 and operating room 7, each shown in FIG. 1 in block diagram form. Valve 22 is correspondingly opened to allow gas flow from output tube 23 to vacuum tubing 24. Once the valves are open, vacuum pump 25 is activated to draw an air sample into chamber 16 through input tube 29. Once the sample is fully drawn into chamber 16, all the valves are closed and the sample is tested to determine in what quantities it contains the vapors of interest.

Infrared (IR) source 11 generates an infrared beam 12 which exits the source 11 and reflects off the first of flat mirrors 13 through infrared window 14 into test chamber 16. Concave mirrors 15 are positioned in such a way that the IR beam 12 entering test chamber 16 is reflected between the mirrors 15 approximately forty times before exiting through a second IR window 14. The mirrors 15 are angled in such a fashion as to allow these multiple reflections of the beam as it gradually works its way across the test chamber 16 before exiting through the second IR window 14. Upon exiting the chamber, the IR beam reflects off the second of the flat mirrors 13 and is directed into infrared detector system 18. An acceptable IR source and detector is the FTIR Spectrometer sold by MIDAC Corporation.

The IR detector 18 detects a decrease in light intensity for various wavelengths of interest. This reduction in magnitude is caused by the absorption of the light at selected wavelengths by certain vapor elements in the test chamber 16. As the light travels through the test chamber 16, different wavelengths are absorbed by different gaseous elements. Hence, the spectrum of the beam 12 exiting the test chamber 16 is an indicator of the presence of certain vapors of interest in the chamber 16. The multiple reflections of the beam 12 through the test chamber 16 allows the beam to pass through more of the vapor sample, increasing the probability of absorption, and therefore increasing the sensitivity of the test chamber 16. The chamber is approximately one foot long, and with forty reflections in the chamber 16 an overall path length of about ten meters is obtained.

Once testing of the sample is complete, the detection data from IR detector 18 is converted to electrical signal impulses and output along line 21 to bidirectional connector 31.

Upon successful completion of the testing of the air sample, a new sample must be brought into test chamber 16. But before a new sample can be tested, the old sample must be removed, and the test chamber must be purged. The purging of the chamber 16 guarantees that no traces of the old sample are left behind in the chamber to cause an errant reading in the vapor detector.

Purging in the present embodiment may be accomplished by drawing a fixed quantity of air from the new sampling location through the test chamber 16. A sample quantity of approximately ten times the volume of test chamber 16 adequately removes any lingering traces of the previous sample. With the test chamber having a volume of approximately 2.7 liters, this requires a purging volume of 27 liters to be drawn through the chamber 16.

The air monitoring unit 10 is centralized and services a number of different sample locations through control of input valves 27 leading to sample input ports 26. Tubing leads from input ports 26 to the sample locations and the distance from the unit to the sample location may be as much as 500 feet. Such a lengthy distance means a relatively slow flow rate, and hence a purging time much longer than that for a sample taken from a closer location. An optional input vacuum line 28 uses a vacuum pump or source (not shown) to keep conduits to ports 26 purged, but due to greater flow restriction, flow may still be relatively slow for the longer distances. Depending on the application, it is possible to use a test chamber with a smaller volume, thereby reducing the purge volume and the purging time. Unfortunately, this also means a shorter path length through the test chamber 16 for the IR beam 12, and thus a reduced sensitivity in the detector 18. A method of reducing the purging time is discussed below.

The flow of gas in and out of chamber 16 is controlled by valve controller 20. Valve controller 20 is part of the data processing system of the environment monitoring system, and controls some or all of the activities of the gas monitoring unit 10. When a purging cycle is required, valve controller 20 opens the appropriate electrically controlled valves, and turns on the appropriate vacuum pumps. For an ordinary purge cycle, valve controller 20 opens valve 22 to allow gas flow through outlet tube 23 and vacuum tubing 24. The valve controller 20 also opens the appropriate input valve 27 and valve 41 to allow gas flow from the selected input sample port 26 to the sample chamber 16. The valve controller thereby turns on the vacuum pump 25 connected to vacuum tubing 24 such that a new gas sample flows into chamber 16 while the old sample is drawn out through outlet tube 23. When the appropriate volume of gas has been drawn through the chamber 16 and the appropriate pressure has been reached, the valve controller 20 closes the valves and initiates the test cycle.

The valve controller 20 may draw purge gas for different durations of time depending on the length of conduit to each sampling station. The amount of purging required may be determined during set up of the system by drawing a quantity of known test gas from each station. The purging can be held to a minimum.

An alternative purging cycle involves the use of vacuum pump 32 and a chamber 34. The chamber is first evacuated by the pump 32. At the initiation of a purging cycle, valve controller 20 opens the same valves at the input side of the test chamber 16 as were opened for the ordinary purge cycle. On the output side, however, valve 22 is opened such as to allow gas flow from outlet tube 23 to chamber 34. There is a rapid transfer of gas from the test chamber 16 to the larger evacuated chamber 34. Thus, the purging time may be decreased for a particular sample by decreasing the amount of purging required.

Pump 40 may be provided to increase the sensitivity of the system if higher sensitivity is required or if it becomes necessary to reduce the volume of test chamber 16. The pump 40 may be a long piston pump or it may be a vacuum and pressurized gas driven bladder pump. While a sample is being tested in test chamber 16, valve controller 20 opens the valve 27 which corresponds to the next sample location. Valve 41 is also activated such that gas flow is allowed between the next sample location and pump 40 while preventing gas flow to input tubing 29. Valve controller 20 then starts pump 40 so that a new sample is drawn. The two valves are then closed and upon completion of the testing of the gas sample in the test chamber 16, valve controller 20 initiates a purging cycle. When the purging cycle is complete, the valve controller activates valve 41 such that gas flow is allowed from pump chamber 40 to test chamber 16. The valve controller then starts the pump 40 in a reverse direction such that the new gas sample is forced into test chamber 16. Utilizing pump 40, the pressure in test chamber 16 may be raised from 2 to 10 times the normal chamber pressure. Since the volume of sample gas in the test chamber is then much larger than under ambient pressure, the IR beam passing through the chamber passes through a proportionally larger quantity of gas. Thus the opportunity for the light to be absorbed is greater and so is the sensitivity.

Input port 38 and valve 36 of gas monitoring unit 10 allow a test gas to be introduced directly into test chamber 16. This provides a means by which the detection unit may be tested without having to draw a sample through input tubing 29 for calibration of the unit.

In addition to valve controller 20, an extension of the data processing system is provided to allow a higher level of system control. The IR detector 18, the IR source 11, and the valve controller 20 each include a bidirectional signal line indicated 21, 30, and 33 respectively. Each of these is accessible to a host computer through connector 31 and bidirectional cable link 56.

Figure 2:
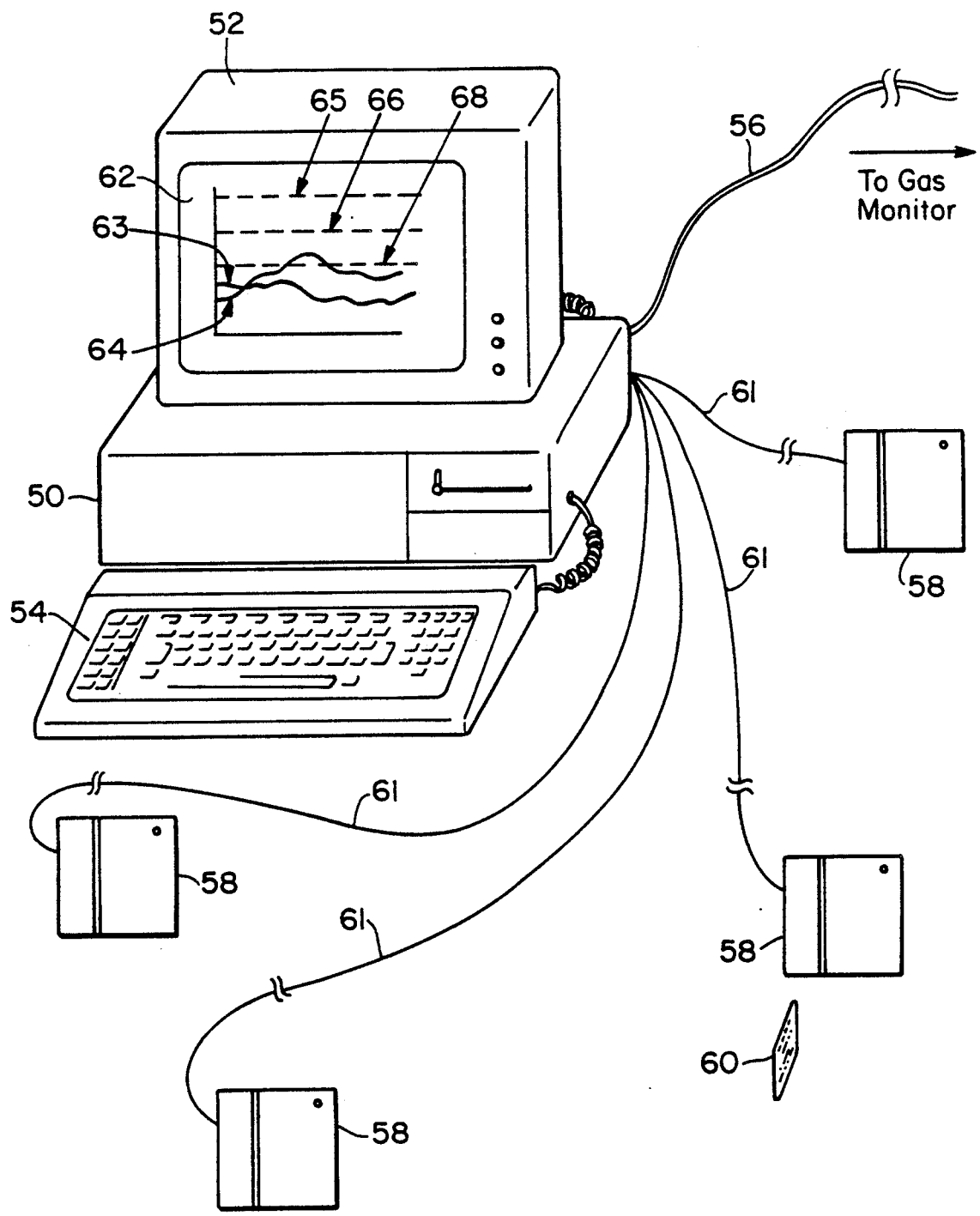
FIG. 2 shows the host computer of the data processing unit with monitor, keyboard, and magnetic card readers.
Figure 3:
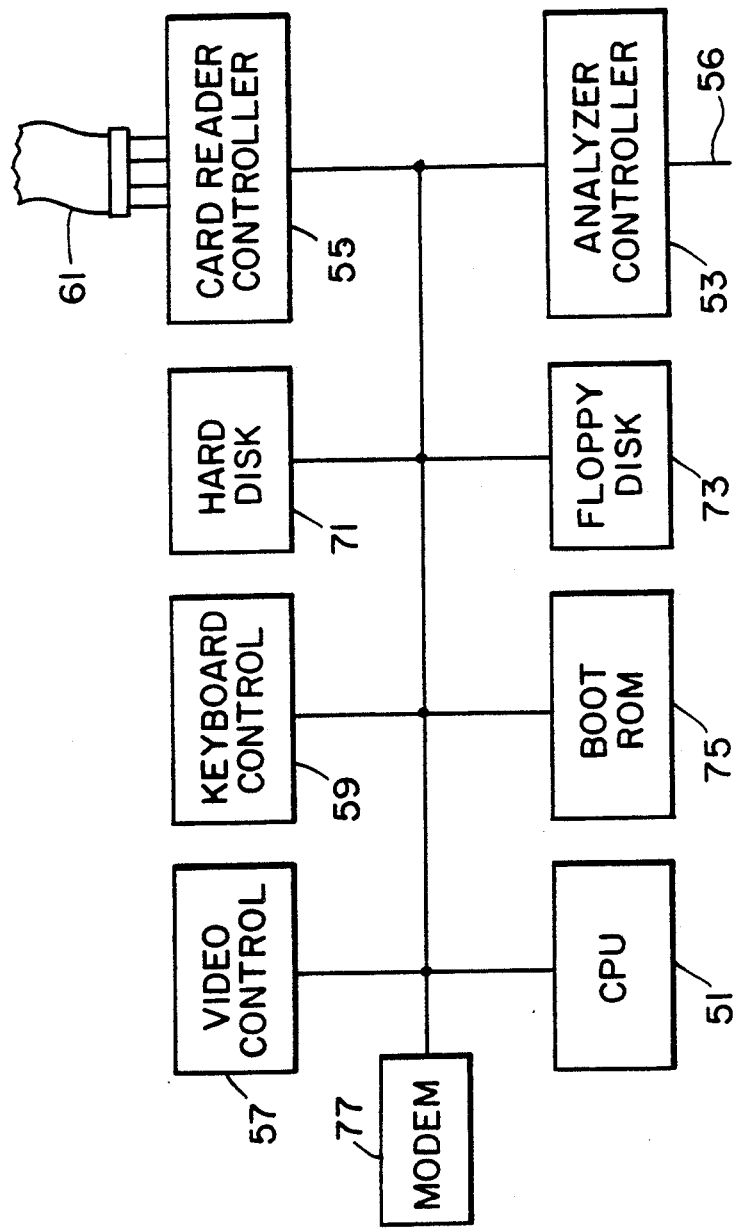
FIG. 3 is a block diagram of the computer of FIG. 2.

FIG. 2 shows a host personal computer (PC) 50 with accompanying monitor 52 and keyboard 54, and FIG. 3 is a block diagram of the PC. Bidirectional link 56 provides a communication path between the central processing unit 51 of the PC and the gas monitor 10 of FIG. 1 through the controller 53. The PC 50 runs a software program which may, for example, be based on the Spectra Calc package offered by Galactic Industries Corporation of Salem, N.H. That basic software is supplemented to included features discussed below. The PC 50 and the microprocessor based valve controller 20 of FIG. 1 together comprise a data processing unit capable of controlling all the functions of the environment monitoring system. A preferred embodiment of the present invention samples vapors in the rooms of a hospital, but the system is equally capable of monitoring any large scale multiple room environment.

Besides controlling system operation, the data processing system of the present invention stores different types of pertinent information. Typically, a hospital has many employees who work a variety of different shifts in different parts of the hospital. To monitor the exposure level of hospital personnel to various levels of potentially hazardous vapors, it is necessary to keep a record of how long they are in contact with these vapors and at what level of exposure. Thus, the data processing unit not only records measurements from different sample locations, but keeps track of which personnel are present in which location. The data processing unit accepts identification inputs recording the presence of each employee in a certain location by individual employee number.

In FIG. 2, a number of magnetic card readers 58 are shown, each card reader corresponding to a different sample location. Each card reader is in communication with PC 50 through cable 61 and a controller 55. An employee checks in and out of any particular sample location by passing an identification card 60 through the card reader 58. The identification information is relayed to the data processing unit which records the length of time that each employee is in each sample location. Thus a complete exposure record is automatically made on each employee to provide a warning of high cumulative exposure over any period of time. An alternative to the card reader is a keypad by which each individual could enter a personal code.

Figure 4:
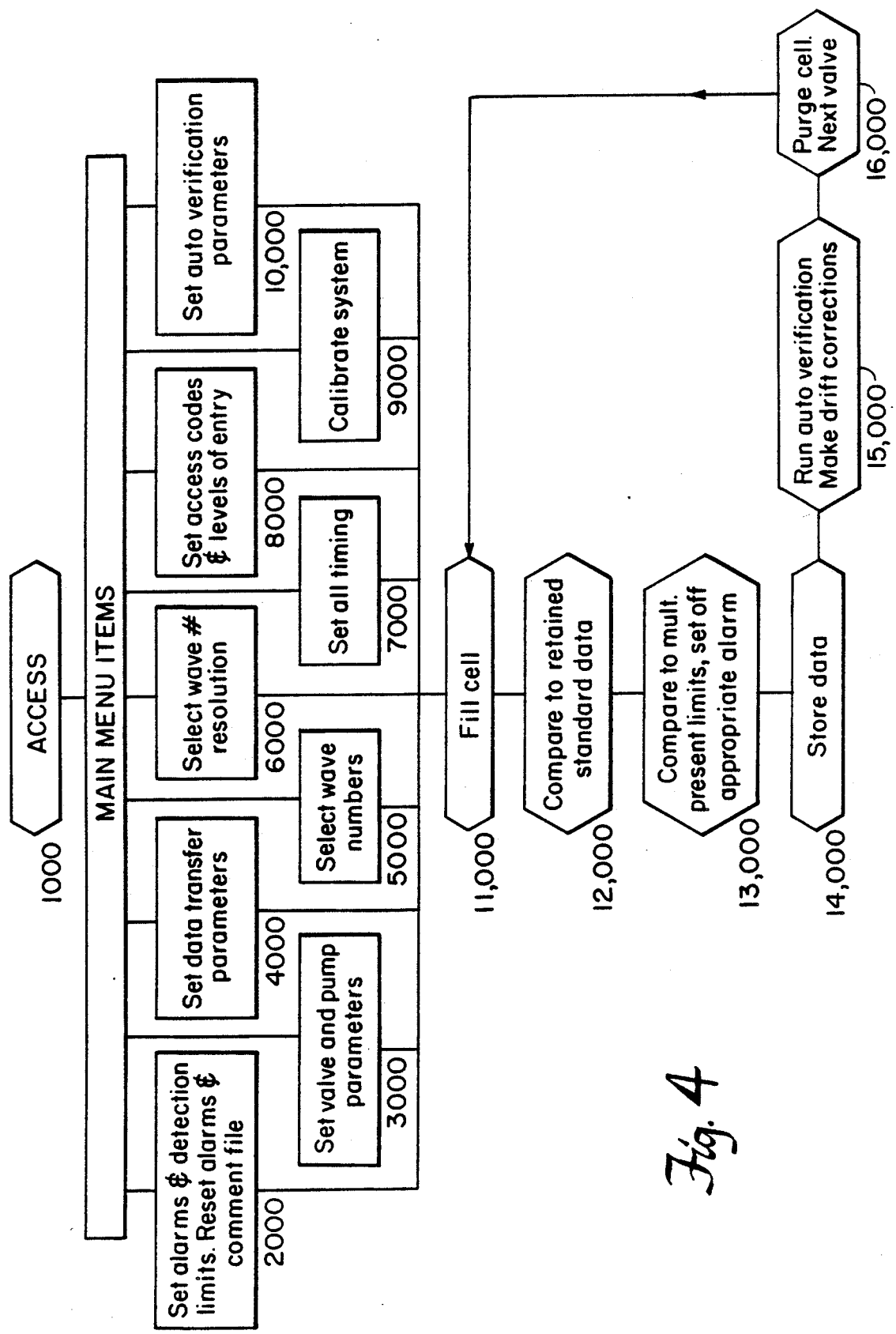
FIG. 4 shows a breakdown of the software controlling the data processing unit.

A flowchart breakdown of the software used for the data processing unit is shown in FIG. 4. Level 1000 is the level of software which controls access to the system. Because there may be a number of different users operating the data processing unit, it is necessary to protect the system software from tampering or vandelism. The access program prohibits a user from accessing the software control systems without the proper entry code. Access may also be granted by the reading of an access code on an individuals identification card 60 using a card reader 58. Multiple levels of access may be used to restrict certain personnel from some of the control systems while granting access to others.

The main menu items of FIG. 3 show the control systems of the data processing unit which are available to user control. Level 2000 controls system alarms and detection limits. Different types of alarms are provided with the process environment monitoring system which indicate that the quantity of a hazardous gas in a sample location has reached a certain threshold. The present embodiment uses a three-level alarm system. The first level is a low-level alarm which is issued locally in the process environment to indicate that the quantity of a certain gas in a sample location in unusually high. This type of alarm might issue if there was an accidental leak of anesthesia gas caused, for example, by a loose mask on a patient, loose tubing or a valve accidentally left open. The low-level alarm provides detection of this condition and allows time to investigate the situation so that it is not necessary for all personnel to immediately leave the room.

The next level of local alarm is triggered when the concentration of harmful vapor reaches an even higher threshold than that of the low-level alarm. Upon reaching this level an additional alarm would be issued to a remote location such as to a system operator or directly to service personnel. Such an alarm indicates that the quantity level of a harmful vapor in a sample location is high enough to warrant immediate action by a system operator or a hospital administrator.

The highest alarm level is the critical alarm level. The critical alarm issues an alert on both a local and remote level to indicate that the gas level is dangerously high and that immediate action such as evacuation is required. The alarm might be in an audible form in the process environment so that it is not overlooked.

In FIG. 2, the screen 62 of monitor 52 shows a possible display output which graphically illustrates the level of two different gases in a process environment. Traces 63 and 64 shown on screen 62 are representations of the quantity levels of two different gases being monitored in the process environment. The quantity level is shown as being plotted versus time, and if monitor 52 is a color monitor, the traces 63,64 can be two different colors. Also indicated on the screen display are alarm level thresholds 68, 66, and 65 which correspond to the low-level alarm, the remote alarm, and the critical alarm respectively. This allows the gas levels to be continuously monitored by a system operator. If the two gases being monitored have different threshold levels, the traces are normalized by the data processing unit to show a relative toxicity level. The system may be run twenty-four hours a day for continuous monitoring. However, to prevent damage to the screen, it is best that the monitor not be turned on unless user interface is required. Therefore, the CPU may disable the video controller 57 during routine monitoring operation. The monitor may be turned on by the CPU in the event of an alarm limit being reached, by a card being input to a reader, or by input from the keyboard through a keyboard controller 59. When turned on, the video controller 57 periodically scrolls or shifts the data on the screen. In the event that the monitor is left on for an extended period of time, this scrolling helps to prevent the phosphorous screen from becoming burned from long term illumination of a static image on the cathode ray tube of the monitor.

System level 2000 of the data processing unit controls the alarms and is restricted to high access personnel only. This element of system control allows trigger levels for the different alarms to be set at varying thresholds for different absorption wavelengths. This allows alarms to be triggered at different exposure levels for different gases. Within this level an operator may also reset alarms and enter a comment to the data processing unit for storage and later report use. This comment may be a record as to the nature or cause of an alarm.

System level 3000 allows the system operator to set pump and valve parameters to be executed by the valve controller 20. These parameters include setting the selection of the sample location and adding or subtracting a number of monitoring lines. A program is also available to optimize the valve opening time for each selected location. The order of room selection must be indicated as well as the nature of any purging which must be performed. If a fast purge or a pressurizing of the cell is desired, it may be input on this level.

System level 4000 involves the data transfer parameters of the data processing unit. This control level is flexible and must be customized to the requirements of the individual application. Inputs on this level include instructing the data processor as to what data to store as well as when and how to transmit the data. If reports on the data are to be generated periodically, a system operator sets up what will go in the reports and when the reports will be generated.

System level 5000 allows a user to select the wave numbers to be looked at for each test location. Selection of the elements to be monitored is thereby accomplished on this level.

System level 6000 allows the wave resolution to be selected for each element under test. Increasing the wave resolution increases the discrimination between different peaks of the detected wavelength spectrum.

System level 7000 receives input parameters for controlling system timing. Among these parameters are how often to sample a test location, how long to collect a particular sample, and how long to purge a new sample gas through test cell 16 to provide an optimal reading. Working in conjunction with valve controller 20, this system level serves as a flow controller to control the timing and flow of samples through the different conduits leading from the sample location to test cell 16.

Level 8000 allows the access parameters of the system to be set. This includes setting the access codes for all the users of the system. To ensure complete control of the access system, a modified ROM is installed in the computer to prevent any tampering with the access system. Multiple levels of access must be coordinated with the access codes of all users. If desired, this system supports the reading of a magnetic card or badge or requires a personal code to be entered on a keypad or the keyboard 54. Unless a proper authorization code is entered into the system, input through the keyboard or floppy disc or a modem may be inhibited.

System level 9000 involves the calibration of the system. By comparing IR readings for a clean test sample and a controlled test sample, appropriate calibration data is recorded.

System level 10,000 allows a user to input how often and by what parameters an automatic verification procedure should be run. The verification procedure may check any of the electronic and mechanical components of the system. For example, using feedback from pressure transducers, proper operation of various valves may be checked. Also, where a system fault is recognized, an override may present alarm indications. The automatic verification procedure may include the input of a known sample quantity of a test gas to verify the proper operation of the environment monitoring system.

System levels 11,000–16,000 concern the actual functional procedures of the test system. The selection of the steps outlined by these levels and the order in which they are performed is dependent on the parameters selected in the main menu items 2000–10,000.

Level 11,000 controls the filling of the sample cell 16. A sample is drawn into the cell until all readings stabilize. The control parameters of the test duration, whether to use a vacuum, and whether or not to pressurize the cell are all set ahead of time.

Level 12,000 compares the raw data from the current sample with retained standard data to determine a value in meaningful units for each previously selected wave number.

Level 13,000 compares the data from level 12,000 with previously set threshold limits and initiates any appropriate alarm sequence.

Level 14,000 stores the data from the test in accordance with the established structure of the data processing unit.

Level 15,000 controls the auto verification cycle. The data from the cycle is checked to see if the system is operating correctly, and makes any neccessary drift corrections. If the system is not functioning properly, inappropriate alarms are shut off, the auto verification alarm is triggered, and the problem is recorded in data storage. Any apparent drift is analyzed and correction is made to the appropriate calibration data.

Level 16,000 is the final step in the procedure, controlling the change of the test sample. The input valve is changed to the next selected room, and the cell is purged. Control is then returned to level 11,000 as indicated in the flow chart of FIG. 3.

The different levels of access can be referred to with regard to storage units of different access levels. All high level access operations such as the altering of system parameters or access codes are kept in an inaccessible hard disc storage unit 71 which prevents access by any but those with high level access privileges. An accessible floppy disc storage unit 73 is also provided, however, to allow for updating of the software and to allow operators of lower level access privileges to control routine operations and input data to the system. Also of importance is the rerouting of system start-up control. The ordinary PC operating system is replaced with a customized boot ROM 75. The ROM causes the system to immediately call the environmental monitor software rather than software stored on any floppy disc. This precaution dedicates the otherwise conventional PC to the monitoring functions and prevents conflicting uses of the system. This approach also prevents tampering with the operating system of the PC which could change system parameters or access priorities.

A modem 77 allows for communications with a central office. For example, data may be forwarded to the system supplier for more detailed analysis. An authorization code must be provided to gain access to the system.

While this invention has been particularly shown and described with references to preferred embodiments thereof, it will be understood by those skilled in the art that various changes in form and details may be made therein without departing from the spirit and scope of the invention as defined by the appended claims.

We claim:

1. In a process environment monitoring system, a method of testing gas from a process environment comprising:

drawing a sample of gas from the process environment into a test cell;

identifying gas in the test cell with a gas analyzer;

evacuating a volume which is larger in size than the test cell;

after identifying said gas, opening fluid communication between the test cell and the evacuated volume such that said gas is rapidly drawn from the test cell to the evacuated volume to clear the test cell; and drawing purge gas through the test cell to substantially replace gas in the cell with purge gas.

2. The method claimed in claim 1 wherein the purge gas is drawn from the process environment.

3. The method claimed in claim 1 wherein the evacuated volume is between four and ten times a volume of the test cell.

* * * * *